(12) United States Patent
Zemer et al.

(10) Patent No.: US 9,046,476 B2
(45) Date of Patent: Jun. 2, 2015

(54) METHOD AND SYSTEM FOR THE DETECTIONS OF BIOLOGICAL OBJECTS

(75) Inventors: Dan Zemer, Rehovot (IL); Oz Bornstein, Ramat Hasharon (IL)

(73) Assignee: VBACT LTD., Rehovot (IL)

(*) Notice: Subject to any disclaimer, the term of this patent is extended or adjusted under 35 U.S.C. 154(b) by 0 days.

(21) Appl. No.: 13/701,679

(22) PCT Filed: May 31, 2011

(86) PCT No.: PCT/IL2011/000421
§ 371 (c)(1),
(2), (4) Date: Dec. 3, 2012

(87) PCT Pub. No.: WO2011/151820
PCT Pub. Date: Dec. 8, 2011

(65) Prior Publication Data
US 2013/0071875 A1    Mar. 21, 2013

Related U.S. Application Data

(60) Provisional application No. 61/350,133, filed on Jun. 1, 2010.

(51) Int. Cl.
*G01N 21/25* (2006.01)
*G06F 17/30* (2006.01)
(Continued)

(52) U.S. Cl.
CPC ............ *G01N 21/25* (2013.01); *G01N 15/1475* (2013.01); *G06T 7/0012* (2013.01);
(Continued)

(58) Field of Classification Search
CPC ............ G06F 17/30595; G01N 21/25; G01N 15/1475; G06T 7/0012; G06T 2207/10048; G06T 2207/10056; G06T 2207/30024
USPC ................... 435/34, 288.7; 382/128; 707/736
See application file for complete search history.

(56) References Cited

U.S. PATENT DOCUMENTS

| 5,473,706 A | 12/1995 | Bacus et al. |
| 2006/0039593 A1 | 2/2006 | Sammak et al. |
| 2006/0280352 A1 | 12/2006 | Muschler et al. |

FOREIGN PATENT DOCUMENTS

| WO | 96/37797 A1 | 11/1996 |
| WO | 9637797 A1 | 11/1996 |

(Continued)

OTHER PUBLICATIONS

Freitas, Nanomedicine, vol. I: Basic Capabilities, Landes Bioscience, Georgetown, TX, 1999, Accessed online at: www.nanomedicine.com/NMI/8.5.1.htm.*

(Continued)

*Primary Examiner* — Karen Cochrane Carlson
*Assistant Examiner* — Jennifer M. H. Tichy
(74) *Attorney, Agent, or Firm* — Browdy and Neimark, PLLC

(57) ABSTRACT

The present invention provides a method for identifying biological objects on a substrate; the method comprises: (i) illuminating the substrate carrying the biological objects with a light beam; (ii) acquiring at least one optical image of the illuminated substrate; the light beam comprises a wavelength band, the wavelength band is selected to induce at least one optical aberration in the optical image of the illuminated substrate; the optical aberration is predetermined as characterizing the biological objects; and (iii) processing said at least one optical image to provide a value or a combination of values indicative of presence or absence of said at least one optical aberration; said value or combination of values permitting detection or identification of the biological objects on said substrate. The invention also provides a processing unit, a system and a database for use in connection with the method of the invention.

25 Claims, 12 Drawing Sheets

(51) Int. Cl.
*G06T 7/00* (2006.01)
*G01N 15/14* (2006.01)

(52) U.S. Cl.
CPC .............. *G06T 2207/10048* (2013.01); *G06T 2207/10056* (2013.01); *G06T 2207/30024* (2013.01); *G06F 17/30595* (2013.01)

(56) References Cited

FOREIGN PATENT DOCUMENTS

| WO | 03102210 A2 | 12/2003 | | |
|---|---|---|---|---|
| WO | 2005080944 A1 | 9/2005 | | |
| WO | WO 2007/064313 | * | 6/2007 | ............... A61K 9/70 |

OTHER PUBLICATIONS

University of Maryland, BSCI 223-General Microbiology, List of Lecture Topics, Comparison Between Prokaryotic and Eukaryotic cells, Apr. 16, 2002, Accessed at: www.life.umd.edu/classroom/bsci424/BSCI223WebSiteFiles/ProkaryoticvsEukaryotic.htm.*
Sekar et al., Fluorescence resonance energy transfer (FRET) microscopy imaging of live cell protein localization, The Journal of Cell Biology, (Mar. 3, 2003), vol. 160, No. 5, pp. 629-633.*
Wang et al., Multicolor FRET Silica Nanoparticles by Single Wavelength Excitation, Nano Letters, (2006), vol. 6, No. 1, pp. 84- 88.*
Wikipedia, Forster resonance eneregy transfer, Accessed Jan. 22, 2014, Online at: en.wikipedia.org/wiki/F/%C3%B6rster_resonance_energy_transfer.*
International Search Report: Application No. PCT/IL2011/000421, European Patent Office, Nov. 11, 2011, Rijswijk, Netherlands.

* cited by examiner

METHOD AND SYSTEM FOR THE DETECTIONS OF BIOLOGICAL OBJECTS

FIELD OF THE INVENTION

This invention relates generally to imaging methods and systems for detecting and identifying objects in a biological sample.

BACKGROUND OF THE INVENTION

Various imaging techniques have been developed and employed for imaging and detection samples or micro objects. These techniques are typically aimed at improving the detection and imaging of cellular objects such as bacteria, tissue portions and alike.

Microscopes making use of digital camera are now available. These typically use a CCD camera to examine a sample, and the image can thereafter be shown directly on a computer screen without the need for optics such as eye-pieces.

One such technique is disclosed for example in WO96/37797 including a microscope system having a wide field of view optical system, a detector positioned to record 15 an image of an object from the optical system, and a computer. The optical system is relatively monochromatic and adjustable in response to the signals provided by the computer to focus the image of the object at a wavelength that is selectable from a range of wavelengths while the light delivered to the detector is limited to the selected wavelength. By superposing successive images at different selected wavelengths, an image or composite data 20 set at multiple wavelengths is produced. The microscope system utilizes a lens system (reflective, refractive or a combination thereof) that produces an aberration-free image.

SUMMARY OF THE INVENTION

In one of its main aspects, the present invention provides method for identifying biological objects on a substrate, the method comprising:
  illuminating the substrate carrying the biological objects with a light beam;
  acquiring at least one optical image of the illuminated substrate; the light beam comprises a wavelength band, the wavelength band is selected to induce at least one optical aberration in the optical image of the illuminated substrate; the optical aberration is predetermined as characterizing the biological objects; and
  processing the at least one optical image to provide a value or a combination of values indicative of presence or absence of the at least one optical aberration; the value or combination of values permitting detection or identification of the biological objects on the substrate.

In another aspect, the present invention provides a processing unit for identifying a biological object in a sample, comprising:
  input module configured and operable to receive data corresponding to an optical image of a substrate supporting the sample; and
  a processor configured and operable to process the data corresponding to the optical image and to provide a value or a combination of values indicative of presence or absence of at least one optical aberration pre-determined as characterizing the biological object; the value or combination of values permitting identification of the biological object.

In another aspect, the present invention provides a processing unit for determining at least one illumination condition to induce a desired optical aberration in an imaged biological object in a sample, comprising:
  input module configured and operable to receive at least one parameter of the biological object, the at least one parameter is associated with the desired optical aberration; and
  a processor configured and operable to process the at least one parameter of the biological object to provide the at least one illumination condition that matches the desired optical aberration, the at least one illumination condition is capable of inducing the desired optical aberrations in the imaged biological object.

In yet another aspect, the present invention provides a system for identifying biological object in a sample, comprising:
  a light source configured and operable to illuminate the sample;
  an image capturing component configured and operable to acquire at least one optical image of the sample;
  a processor configured and operable to process the optical image, and to provide a value or a combination of values indicative of presence or absence of at least one optical aberration pre-determined as characterizing the biological object; the value or the combination of values permitting identification of said biological object.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3A is an image of *E-coli* DH5Alpha (straight arrow) and *Pseudomonas Aeruginosa* (broken arrow) mixed with filtered water and imaged on transparent membrane filter with optical microscope at ×40 magnification. The medium is illuminated with green color filter. Image shows differences in bacteria dimensions, contour and contrast level surrounding the bacteria and contrast levels within the bacteria body which allows distinction between the two bacteria and further detection and identification of the two bacteria;

FIG. 3B is an image of *E-coli* DH5Alpha (in bottom left circle) and *Klebsiella Oxytoca* (in upper right circle) mixed with filtered water and imaged on transparent membrane filter with optical microscope at ×40 magnification. The medium is illuminated with blue color filter. The difference between the two bacteria is demonstrated in several parameters: bacteria dimensions, bacteria body color, hue and uniformity of contrast and the contrast level surrounding the bacteria; FIG. 3C is an image of *Bacillus subtilis* (bottom left) and *Pseudomonas aeruginosa* (upper and right bacteria) mixed with water and imaged on transparent membrane filter with optical microscope at ×40 magnification. The medium was illuminated with UV filter. The difference between the two bacteria is demonstrated by the color of bacteria outline and the hue of the bacteria internal body.

DETAILED DESCRIPTION OF SOME NON-LIMITING EMBODIMENTS

Figure 1A:
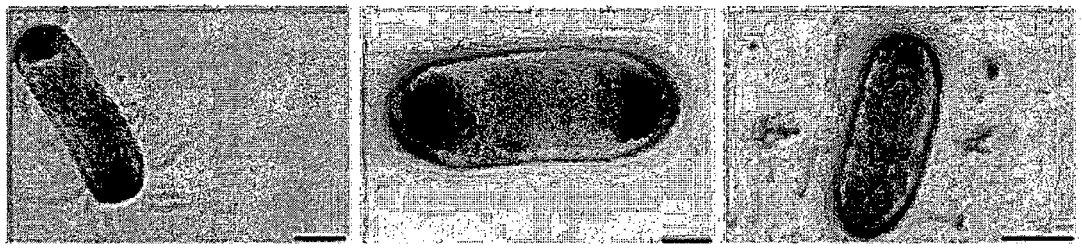
FIG. 1A is an image of *E-coli* bacteria taken by transmission electron microscope with nano-metric resolution (The EMBO Journal (2008) 27, 1134-1144).

The present invention is based on the finding that biological matter, such as microbial cells, may be characterized by optical aberrations of their optical images and that these optical aberrations, once identified as a biological object characteristic, can be used for qualitative as well as quantitative determination of the presence of the biological object in a tested sample. Further, it has been found that different optical aberrations can be induced by illuminating the biological matter in the sample with a light beam pre-determined as inducing a desired optical aberration.

Thus, in accordance with a first of its aspects, the present invention provides a method for identifying biological objects on a substrate carrying said biological objects comprising:

illuminating the substrate with a light beam comprising a wavelength band selected to induce, in an optical image of the biological objects, at least one optical aberration pre-determined as characterizing the biological objects; acquiring at least one optical image of the illuminated sample;

processing said at least one optical image to provide a value or a combination of values indicative of presence or absence of said at least one aberration; said value or combination of values permitting identification of the biological objects in said sample.

In the context of the present invention, the substrate carrying the biological object is preferably a solid substrate. The term "biological object" which may be used herein interchangeably with the term "biological matter" is used to denote any biological material having an average size ranging from between about 0.4 µm to about 200 µm, at times from between about 1 µm to about to 100 µm, and even, at times, from about 1 µm to 20 µm.

In one embodiment, in order to facilitate the method of the invention, the combination of the biological objects on the substrate is transparent, translucent, semi transparent or semi translucent.

In one further embodiment, the biological object is a cellular matter and includes a single cell, a collection of cells (e.g. a tissue) as well as parts of cells that have at least the above defined average size. In this context, the cellular matter may be eukaryotic as well as prokaryotic cellular matter.

When referring to eukaryotic cellular matter, it is to be understood as encompassing animal, fungal as well as plant cells. In one embodiment, the eukaryotic cellular matter is cellular matter being present in bodily fluids, such as, without being limited thereto, saliva, blood, urine, cerebrospinal fluid.

When referring to prokaryotic cellular matter, it is to be understood as encompassing microbial cellular matter. A non-limiting list of microbial cells that may be identified in accordance with the invention comprises, *Escherichia Coli, Chlamydia, Salmonella, Pseudomonas, Klebsiella, Staphylococcus*, or *Streptococcus*. Following a list of some non-limiting micro-organisms which may be detected and/or identified by the method of the present invention:

Protozoas: *Acanthamoeba; Balantidium coli; Blastocystis; Cryptosporidium; Cyclospora cayetanensis; Entamoeba histolytica; Giardia intestinalis; Isospora belli; Microsporidia; Naegleria fowleri; Toxoplasma gondii.*

Bacteria: *Acetobacter Melanogenus; Acinetobacter; Actinomyces israelii; Aeromonas; Alkaligenes; Bacillus; Brucella; Burkholderia; Campylobacter; Cardiobacterium; Chlamydia; Clostridium; Coxiella burnetii; Enterobacter sakazakii; Enteroccous; Erwina aroideae; Escherichia coli; Helicobacter; Klebsiella; Legionella; Leptospira; Listeria monocytogenes; Moraxella; Mycobacterium; Naegleria fowleri; Non-tuberculous mycobacteria; Pasteurella pestis* (plague); *Pseudomonas; Rickettsia; Salmonella; Serratia; Shigella; Staphylococcus; Streptococcus; Tsukamurella; Tularemia; Vibrio cholerae; Yersinia enterocolitica*; and subspecies of each.

Fungi: *Absidia corymbifera; Acremonium* spp.; *Alternaria alternate; Aspergillis* spp.; *Aureobasidium pullulans; Blastomyces dermatiitidis; Botrytis cines; Chaetomium globosum; Cladosporium* spp.; *Coccidioides immitis.*

In yet another embodiment, the biological objects comprise viruses chemically or biologically linked to carrier, the combination of the viruses with the carrier having an average size within the above defined range. The carrier may include without being limited thereto, micro-beads/spheres, substrates. Carriers that can be used in accordance with this embodiment may be made of polystyrene, magnetics or paramagnetic matter, glass, mica, silicon, organic (carbon containing) materials and solid chemicals. By way of an illustrative example, the biological object may comprise polystyrene beads attached to a virus or to a biomolecule such as a protein or an antibody, the identification of which is of interest.

In accordance with the method of the invention, the substrate comprising the biological objects is illuminated with a light beam. The light beam comprises a wavelength band or a combination of wavelength bands, the wavelength band comprises at least one wavelength selected from ultra-violet (UV) spectrum to infra-red (IR) spectrum. More specifically, the wavelength band comprises at least one wavelength selected from the group consisting of the infra-red (IR) spectrum, the ultra-violet (UV) spectrum and the visible (VIS) spectrum.

In one embodiment, the wavelength band is a narrow wavelength band, referred to at times, in the art as an optical notch. In the context of the invention, a narrow band or optical notch is used to denote a wavelength band having a width in the range of between about 10 nm to about 100 nm, at times from 10 nm to 50 nm, and at times, even 10 nm to 20 nm.

Optical notches can be produced by notch filters as known in the art. Generally, notch filters provide a narrow wavelength band by passing all frequencies/wavelengths except those in a stop band of a centered frequency/wavelength. For example, Q notch filters are filters which eliminate a single frequency or narrow band of frequencies. Such filters may include, by way of non-limiting, which are commercially available from ONDAX, Inc. (USA) or Iridian Spectral technologies (Canada). The person skilled in the art would appreciate that the present invention can employ other filters such as notch filters to narrow band of frequencies.

Illuminating the substrate carrying the biological objects with a particular light beam of a wavelength band can be also produced by a LED illumination source. The present invention can also employ plurality of such LED illumination source.

The light beam may be a continuous light beam or a continuous string of light pulses. It should be further noted that an image capture can also be obtained by actuating a series or plurality of serial illumination pulses. These pulses are typically synchronized with the camera image acquisition. The light beam typically illuminates the substrate during image acquisition. Illumination may, however, begin before an image is captured.

The collection of illumination conditions required in order to induce a desired optical aberration are referred to herein as "illumination conditions" and these include, without being limited thereto, direction of light from light source to the substrate which may include any illumination side (light from any direction, including upper light, side light and backlight, however, preferably backlight and/or sidelight illumination), illumination intensity, wavelength band(s) of light beam, light source, filters such as notch filters, LED with selected color, micro-optics with prisms.

Illumination conditions can induce optical aberration(s) for a large group of biological objects (e.g. biological family, biological genus). Illumination conditions can more particularly induce optical aberration(s) to a more specific biological class, such as a biological species. The illumination conditions can be collected empirically.

The selection of illumination conditions may depend on the degree of transparency/translucency of the imaged substrate and biological objects. For example, illumination of transparent or essentially transparent biological objects would allow the use of backlight illumination; while illumination of partially (semi) transparent or partially translucent biological objects would include in preference backlight illumination as well as sidelight illumination. Sidelight illumination, in the context of the invention, may include illumination of light from any direction that is 60 degrees or less with respect to the plane of the substrate's surface until essentially parallel to the substrate's surface. Sidelight illumination may allow the capturing of optical aberrations in a biological object's contour and/or in the bacteria's internal organs.

The illumination conditions are selected to induce, in the optical image of the biological objects, at least one optical aberration. As used herein, the term "optical aberration" is to be understood to have the meaning as known in the art, including flaw distortion in the generated image of an optical system such as lens or mirrors as compared to the original image. The optical aberration can also be understood to mean the degradation/departure/reduction of the optical performances of an optical system producing an image of an object being observed (i.e. reduced performance). Classical or conventional optical systems are designed to compensate or even correct for optical aberrations in a projected image. However, the systems, units and/or methods of the present invention are designed to induce an optical aberration in the acquired image, and more particularly, in the imaged matter.

As known in the art, there are six classical types of optical aberrations: astigmatism (where the size and shape of an image variation for different points of focus), chromatic aberration (where various colors of the spectrum are not brought to the same focus and as a result there is an object fringing, i.e. the formation of a colored halo around the imaged object), optical coma, object distortion (where there is a variation in magnification across the visual field), field curvature (where the focus changes from the center to the edge of the field of view), spherical aberration (when using spherical lenses).

In the context of the invention, the optical aberrations are intentionally caused, and these may include any type of distortion in the image. Optical aberrations, may thus include, without being limited thereto, object distortion, image blurring, image vignetting, hue or color shifts or color switch e.g. with respect to the hue or color of the illuminated light; and/or displaced or deformation in shape or size of the imaged object, such as boundaries shift or displacement of at least a portion of the object; and/or changes and enhancement of the contours and internal elements of the biological object. The aberration may be caused with respect to the entire imaged object or to a portion thereof. For example, a colored halo may appear only to a portion of a microbial cell membrane.

As disclosed herein, various biological objects can be distinguished by the type of optical aberration that is caused or induced when illuminating the substrate carrying the biological objects with pre-determined illumination conditions/parameters, such as the wavelength band, the direction of illumination, type of light source, etc.

Accordingly, various biological species or groups of biological species may be cataloged and characterized according to the optical aberration that is induced once illuminated and imaged with predetermined and pre-defined illumination conditions. The combination of one or more specific illumination conditions which results in optical aberrations enables the identification (qualitative and quantitative) of biological object on a substrate. Preferably, the method allows the identification of the specific biological species. The collection of illumination conditions that cause a desired optical aberration for a biological object can be stored on a database, as will be further described below. Thus, the database can be used for data retrieval of illumination conditions for performing the method of the invention. The database can also maintain an optical aberration which characterizes a biological object. The database can thus be used for ascertaining the identity of the biological object by the optical aberration induced for that biological object.

The systems and methods can use a single image or a plurality of images in essentially the same area for the identification of the biological objects on the substrate.

In one embodiment, a single image of the illuminated substrate is acquired. In yet some other embodiments, two or more sequential images are acquired. When acquiring two or more images, these may be obtained with the same or different illumination conditions, e.g. with the same or different wavelength band or notches. For example, a first image may be acquired while applying light with a wavelength band from the UV spectrum, and a second image may be acquired while applying light with a wavelength band from the VIS spectrum. Similarly, the light beam may comprise a combination of optical notches In yet one additional embodiment, the method comprises acquiring in at least two different time points within a pre-defined time window, two or more optical images of said substrate and processing said two or more optical images to obtain therefrom a time dependent value or combination of values indicative of a state of said biological object. This embodiment allows determination of time dependent parameters (state) of the biological objects on the substrate, such as, without being limited thereto, viability, reproducibility, motility, change in shape, motility speed, change in transparency, change in thickness and mutual behavior among biological objects.

Once at least one image is acquired, the method comprises processing of the image that includes optical image data analysis. The image data typically includes pixel information and the image may be presented in any available format, including, without being limited thereto, Tagged Image File Format (TIFF), Joint Photographic Experts Group (JPEG), Graphic Image Format (GIF), Portable Network Graphics (PNG), and Portable Document Format (PDF). Image data can be in a compressed data format or in an uncompressed data format; may relate to any gray or color scale; can include bitmap data, or a portion of a bitmap file containing bitmap data. In one embodiment, image data is generated using a CCD camera.

The image data analysis may be of a single image or of a plurality of images taken for the same area on the substrate with the same or different illuminations, alone or in combination with other aberration inducing conditions (e.g. with the same light beam or two or more light beams characterized by a different wavelength or different wavelength bands, with the same illumination direction of with two or more directions—this refers only to illumination). The processing provides one or more values indicative of the presence or absence of an optical aberration in the image. The presence of the optical aberration (one or more) in the image thereby allows the qualitative and/or quantitative identification of the biological objects on the substrate. The processing includes, in one embodiment, comparing the output value or combination of values with a database comprising pre-determined values that have been a priori determined for optical aberrations that characterize a biological object.

The database can thus be configured to provide functionality such as of an associative container comprising a collection of keys (optionally unique) and a collection of values, where each key is associated with one value or plurality of values. In the context of data structures or databases, "associate" describe the relationship between stored key and value typically referred to as data binding or mapping.

The database can thus associate illumination condition(s) with optical aberration which can be produced thereby. The database can also associate optical aberration(s) with biological objects or classes of such objects including parameters of biological objects such as morphological, structural and behavioral parameters of the biological object. The database can also associate both optical aberration(s) and their corresponding illumination conditions with biological objects or classes of such objects including parameters of biological objects such as morphological, structural and behavioral parameters of the biological object. Therefore, the database can be used to retrieve/store the identity of a biological object in accordance with stored optical aberration or retrieve optical aberration(s) by the identity of a biological object. Further, the database can also be used to retrieve/store illumination condition(s) by optical aberration(s) and vice-versa.

Based on the value or combination of values various decisions are made as to the presence or absence of a biological object on the substrate, if present, the type of biological object (qualitative identification) and/or the amount (quantitative identification) of the biological objects on the substrate. Further, based on the values or combination of values, at least one biological object parameter is obtained. The biological object parameters may include, without being limited thereto, shape, size, dimensions, depth, movement (and movement parameters such as speed, direction), viscosity of the sample carrying the biological object, volume of fluid around the biological object and the respective color and/or contrasts. The biological object parameters can be derived from image analysis procedure performed on an image capture of a sample. The image analysis identifies one or more optical aberration(s) induced in the captured image. The identified optical aberrations are being used by the present invention to implicate that the sample tested comprises a biological object or an object belonging to a particular class of biological objects. In this manner, optical aberrations decide the detection or identification by associating sample content (or the content on a substrate) to the optical aberrations induced therein.

The image analysis can be based on one or more of the common practices such as contour detection, image parameter derivatives, shape detection, image reconstruction, segmentation, image differencing, machine learning and geometric hashing.

As indicated above, the type of biological object may be the identification of any one of the biological species, or even the biological genus, family, order, class, phylum, or kingdom to which the object belongs.

The invention also provides a processing unit for determining at least one condition for inducing a desired optical aberration in imaged biological objects on a substrate comprising:
  an input module configured and operable to receive at least one parameter associated with said desired optical aberration of said biological object; and
  a processor configured and operable to process said at least one parameter to provide therefrom said at least one condition that matches the desired aberration, the at least one condition capable of inducing optical aberrations in said biological objects.

Also provided by the invention is a processing unit for identifying biological object on a substrate, comprising:
  input module configured and operable to receive data corresponding to an optical image of said sample, and
  a processor configured and operable to process said data corresponding to the optical image, and to provide an output value or a combination of output values indicative of presence or absence of at least one optical aberration in said image.

The processing unit for identifying biological object can further be configured and operable to compare said at least one optical aberration with database items. The database items can comprise pre-determined optical aberrations characterizing one or more biological objects or object classes. The processing unit for identifying biological object can further be configured and operable to provide a qualitative output value or a combination of qualitative output values leading to a decision which allows identification of the biological objects on the substrate.

The person skilled in the art would appreciate that output value or output values in the present invention encompasses output signal or output signals indicative of presence or absence of at least one optical aberration in the acquired image.

Also provided by the invention is a system for identifying biological object in a sample, comprising:
- a light source configured and operable to illuminate said sample;
- an image capturing component configured and operable to acquire at least one optical image of said sample;
- a processing unit comprising input module configured and operable to receive data corresponding to an optical image of said sample and a processor configured and operable to process said optical image, and to provide a value or a combination of values indicative of presence or absence of at least one optical aberration pre-determined as characterizing the biological object, and to analyze said value or said combination of values permitting identification of said biological object.

The light source may be configured and operable to provide one or more illumination conditions of the substrate. These may include, without being limited thereto, the type of optical filters such as notch filters for inducing the desired optical aberration characterizing the biological objects to be determined; direction of illumination required to capture the optical aberration characterizing the biological objects, for example, sidelight and/or backlight illumination or a combination of illumination directions; source of light, such as, but without being limited thereto, LED or a selection of LED predetermined in order to induce the desired optical aberration characterizing the biological objects.

The system also includes an image capturing component. The synchronization between operation of the light source and image capturing component may be controlled by dedicated control module that may be an integrated part of the image capturing component or a separate part therefrom. The control module may control, inter aila, the illumination conditions, image capturing resolution, image magnification, aperture dimension, exposure/integration time etc. The image capturing component may be equipped with conventional focus functionalities, such as, without being limited thereto, best contour; Modulation Transfer Function (MTF) measurement/calibration; object detection; triangulation by measurement; close loop image processing—best image. The image capturing component may also include lenses, aperture and shutter.

The image capturing component provides image data for processing by the processing unit. The image data in the context of image analysis is based on a collection of images that essentially cover region of interest (ROI).

The image analysis can be performed by first scanning to collect images from the ROI or portion thereof on the substrate. As indicated above, the image can be acquired using a combination of illumination conditions, such as specific colors, notches or wavelength bands. Then, identification or detection of biological objects can be based on one or more illumination conditions.

In this respect, the present invention can utilize a series or cascade of illumination conditions. In some embodiments, several images are acquired at several corresponding illumination conditions.

The present invention can utilize at least one additional optical condition to induce optical aberrations. In this respect, the present invention can utilize a series or cascade of additional optical conditions. In some embodiments, several images are acquired at several corresponding optical conditions. Each image is processed to identify or obtain one or more optical aberrations. The additional optical condition applied operates in conjunction with the illumination conditions to induce at least one optical aberration in a test sample.

Each image is processed to identify or obtain one or more optical aberrations or values representative thereof. The one or more optical aberrations identified can then be used to deduce the presence or absence of a biological object or to determine the probability (or confidence level) for such presence or absence of a biological object. Alternatively, the one or more optical aberrations or absence thereof can be used to decide that additional image will be acquired being illumination with at least one additional illumination condition. The additional illumination condition is thus used to induce an additional optical aberration, thus producing plurality of optical aberrations or values representative thereof.

The image is being processed with processing parameters selected from initialization parameters which can optionally be stored in database. Processing parameters can also be manually adjusted by a user.

Several modes of operation may be used with respect to the systems and methods of the present invention. Automated as well as manual and semi-automated method can be employed. Manual mode can comprise a user selection of algorithms or adjustments of algorithm parameters. Adjustment can be based on trial and error. Selection of algorithm or its adjustment can further be based in accordance with detection ratio, misdetection ratio, false alarm ratio and any combination thereof. In particular, it can be based of misdetection to false alarm ratio.

The processing unit can communicate with a database module comprising a collection of optical aberrations pre-determined as characterizing biological object as well as other parameters. Information or parameters characterizing a biological object can include morphological parameters, such as: volume, length and/or width of the biological object or any portion thereof. Information characterizing a biological object may also encompass the shape and spatial arrangement and/or interaction (or behavior) of the biological object.

The data/information stored in the database can thus include the biological object (or a part thereof) shape such as but not limited to spiral, rod shape and spherical properties. Additional parameters stored in the database with respect to a biological matter/object can be the width of any of: cell wall, plasma membrane and/or capsule width (or otherwise size).

Spatial arrangement or bacterial behavior one in respect to the other can include the manner by which two or a plurality of biological objects interact or are arranged on a substrate. In this respect, spatial arrangement includes whether the two or more biological objects are arranged in pair, tetrad, hexamer or otherwise. This can also be referred to as mutual arrangement.

Information or parameters with respect to a biological object can also include presence/absence, shape and/or size of an organelle (either membrane bound or not). These also include cellular compartment of the biological object.

Information or parameters with respect to a biological object can also include the position or placement of the biological object including the arrangement of the bacteria structure or organelles.

The information stored in the database can also include relative measurements of the biological objects. The relative measurement can be represented by a ratio of any of the above measurements such as but not limited to length to width ratio of the biological object and surface to volume ratio.

The information stored in the database stated above can include presence, absence or expected values of the biological object or a part thereof. The database can also comprise information relating to expected color ranges of a biological object or a portion thereof.

The database can also comprise information relating to the behavior of a biological object. In respect, behavior includes motility which characterizes the biological object. The behavior can also encompass relative motility of two, three or even a plurality of biological objects. Behavior also includes reproduction of the biological object, its shape and time intervals and/or changes of biological objects morphological parameters over time.

The optical aberrations identified are associated to the expected or otherwise parameters of a biological object. Association includes determination of a biological object parameter when the associated optical aberration is detected. Association should also be understood as confidence level by which the absence or presence of an optical aberration entails the absence or presence of a parameter of a biological object.

These association(s) can be also stored in the database and/or used in accordance with the present invention.

The methods and systems of the present invention can thus induce one or more optical aberrations in a sample. The absence or presence of the induced optical aberrations can therefore be used to determine the absence or presence of a parameter of a biological object. Analysis can include accumulating information about the identity of a biological object in a sample by determining the absence or presence of a parameter of the biological object(s). The more accumulated (or collected) information of parameter(s) of the biological object, the more accurate the identification of a biological matter in the sample is.

In one embodiment, the database provides access to data items stored on a memory; the stored data items associates the biological object or a parameter of the biological object with at least the one optical aberration and/or illumination and optionally other conditions inducing the optical aberration. The database module typically comprises a plurality of entries representing the biological object, each of the entries having at least one associated attribute configured to represent at least one illumination condition and optionally with other conditions capable of inducing at least one optical aberration pre-determined as characterizing the biological object or a parameter thereof; or at least one associated attribute configured to represent an optical aberration of the biological object.

The database module may comprise data items associating illumination conditions, optical aberrations and biological object. The biological object may be identified by its biological specie, biological genus, biological family, biological order, biological class, biological phylum, a biological kingdom and a biological domain of organism.

The database items can be hierarchically modeled in accordance with biological relationship between the groups of biological objects. For example, a specific bacterium can be grouped as a member of a bacteria family. The bacteria family can be grouped with a particular domain. The hierarchy between the groups of biological objects can be based on evolutionary considerations relating to the biological object in question. Alternatively, the hierarchy can be based of empiric data or any other considerations.

Data processing may use a classification module. The classification module can be provided with at least one optical aberration previously induced in accordance with the present invention. The classification module can analyze the optical aberration provided and deduce a selection of possible biological objects being identified. The classifier can optionally communicate with a database as described above. By way of an illustration, a classifier can identify a plurality of possible biological objects.

A classifier can be used to collect parameters or optical aberrations which characterize at least one of the objects in a scanned image. It can also be used to construct a database including the newly identified parameter(s) or optical aberrations with respect to each object.

Reduction of time and execution complexity is typically required. Improved time complexity can be achieved by ranking illumination conditions/parameters and/or optical aberrations as dominant. Reduction of complexity can be realized by limiting the performance of the identification methods to a range of parameters and conditions. Ranking can be performed by providing a matching weighing factor or a degree of dominance/importance to a particular optical aberration. Improved performance can also be achieved by operating the system of the invention on a selected portion of the database. This selection of conditions and parameters may be used to focus image analysis on a group of objects and thus save computation time caused by analysis of irrelevant or insignificant data.

It should be noted that the identification of a single biological object may be a complex process which includes different batches of filters or other illumination conditions. Therefore, optical aberrations identified following the use of a particular batch illumination conditions can be used as criteria for subsequent analysis. For example, optical aberrations identified in a previous analysis can be used to continue the identification process while focusing of a subset of possible biological species. For example, in a biological family level of identification, the results of previous analysis may provide a list of possible best filter(s) selection to be used in a next round of scanning/screening.

As appreciated, the more conditions and/or optical aberrations used in the analysis—the more precise is the identification process. By using a plurality of illumination conditions to induce a plurality of optical aberrations, the risk for misdetection or misclassification is reduced.

As discussed above, the method and system of the invention provide values not only for identification of the biological object, but also values regarding the state of the biological object. In one embodiment, also as described above, this is achieved by acquiring at different time points within a predefined time window, two or more images of the substrate. The two or more images can used to determine a time dependent value or combination of values indicative of a state of said biological object. The values can be obtained by comparing the images acquired at the different time points. As appreciated by those versed in the art, the two timely acquired images may be obtained by the use of a control module or by manually operating the system's components.

The method and system of the invention can require sample preparation, namely, the biological objects within a medium.

Standard microscopic sample preparation can be used in accordance with the present invention. For example, a slide preparation known also by the term "wet mount" slide can be used. Wet mount slide preparations typically utilize a flat slide and a cover slip. To make one, a drop of the sample is placed in the middle of a clean slide and a cover slip is gently placed over the drop at an angle, with one edge touching the slide first. The liquid is then allowed to spread out between the two pieces of glass without applying pressure.

The medium suitable for optical scanning and image acquisition may include, without being limited thereto, any type of fluid, such as water or other liquids, gases, such as air, or transparent or semi-transparent solids. The conditions of the sample may be controlled in terms of temperature, humidity, pressure, sterility, etc., so as to maintain a controlled environment during the operation of the system and assure reproducibility of the identification process.

For image acquisition, separation between the biological objects and the medium is typically required which is achieved by placing the sample comprising the biological objects on a filter and filtering the sample whereby the biological object remains on the filter. Separation may be mechanically, using one or more filters or centrifuge to obtain the sample of biological objects. The sample after filtration may be dry, semi dry or even essentially wet.

The filtered sample is placed on a substrate. At times the filter per se may be used as the substrate. The substrate is typically a transparent, semi transparent, translucent or semi translucent substrate. Substrate transparency can be chosen or constructed based on transparency of a biological object to be suspected to be in the sample and which is to be potentially identified. Biological objects which have transparent to semi-transparent properties would typically be placed on a substrate with similar properties, i.e. transparent or semi transparent substrate, such as polycarbonate or glass. As appreciated, the substrate may be coated with materials to create hydrophilic or hydrophobic properties or adhesive glue for maintaining the biological objects on the substrate. The substrate can be a single layer of a filter or any other transparent material. In case the object being identified is non transparent, the substrate can be either transparent or non transparent material.

The system may be used as a stand alone system or in the form of an array of system units, each system unit configured to operate synchronically, using a central control module. The array of systems may be placed in different locations and the central control module may be used to remotely operate and monitor the operation of the different system units. The control module may be used in a fully automatic mode, partially automatic, or manually.

The system, devices, modules, processor unit can be placed in different environments or on board of several platforms. In particular, the system, devices, modules, processor unit can be positioned onboard airborne, mobilized or naval vessels.

The method and system of the invention may have various applications and as such, may be operated at various locations and monitoring areas where detection of biological objects is described. In one embodiment, the method and system of the invention are used for detection and identification of biological contaminations, such as microbial contaminations in liquids, such as: drinking water and water sources, air contaminations, food contaminations etc.

In some other embodiments, the method and system of the invention may be applicable in medical procedures, e.g. for detection of infecting or undesired biological objects (e.g. cellular matter) in a bodily fluid or in a bodily tissue.

In yet some other embodiments, the system and method of the invention may be used in biological research, e.g. in drug screening, identification of detecting agents for biological objects, affect of chemicals or organic materials on biological objects etc.

As used herein, the forms "a", "an" and "the" include singular as well as plural references unless the context clearly dictates otherwise. For example, the term "a biological object" includes one or more objects which may be the same or different and which are being imaged in accordance with the method and system of the invention.

Further, as used herein, the term "comprising" is intended to mean that, for example, the sample or the substrate includes the biological object, but not excluding other elements, such as acceptable carriers. The term "consisting essentially of" is used to define a sample or substrate which include the biological object but exclude other elements that may have an essential significance on the performance of the method and system of the invention. Embodiments defined by each of these transition terms are within the scope of this invention.

Further, all numerical values, e.g. when referring to conditions, such as illumination conditions, sample composition, object dimension etc. are approximations which are varied (+) or (−) by up to 20%, at times by up to 10% from the stated values. It is to be understood, even if not always explicitly stated that all numerical designations are preceded by the term "about".

The invention will now be exemplified in the following description of non-limiting examples that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

DESCRIPTION OF NON LIMITING EXAMPLES

Sample Preparation:

The samples in the examples were prepared by using ATCC strain of several bacteria. The bacteria in each sample were mixed with filtered water and were placed on a transparent membrane filter from Sterlitech Corporation, USA with pore size of 0.4 μm.

Illumination Conditions and Image Acquisition:

The light used was a halogen light of 30 Wt, with a selected intensity.

The selection of the filter was subjected to the target definition. For each biological object there is an optimal/special filter combination as described in the legends to the figures.

Results:

The images in FIGS. 1B, 1C, 2-3 were obtained with Olympus BX-41 microscope and Olympus Camedia 3030 digital camera with resolution of 3.3 mega pixel. Sterlitech Corporation (USA) Polycarbonate membrane with pore size of 0.4 micron were used as filters.

FIG. 1A is an image of *E-coli* bacteria taken by transmission electron microscope with nano-metric resolution (The EMBO Journal (2008) 27, 1134-1144). This image is used in the present context a reference for comparison purposes alone. As shown below, the images in FIGS. 1B, 1C, 2 and 3 obtained with Olympus BX-41 microscope can be used in accordance with the present invention to detect or identify parameters of a biological object.

Figure 1B:
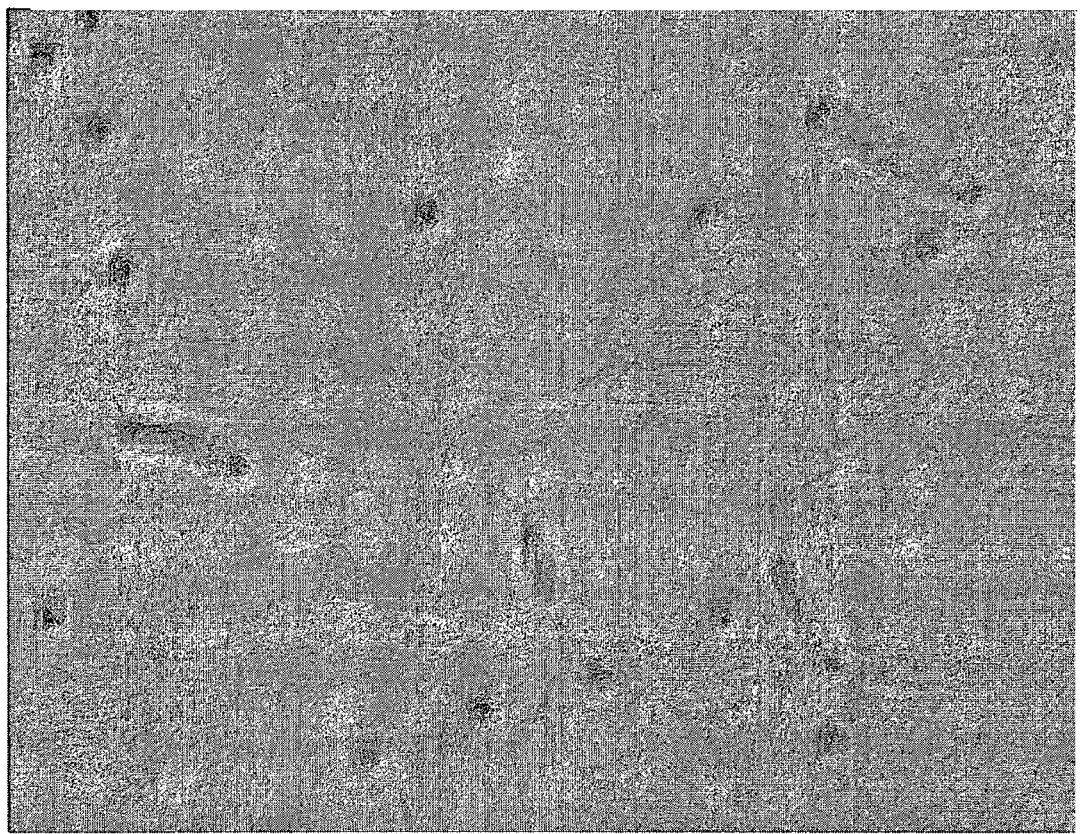
FIG. 1B is an image of *E-Coli* images were taken with Olympus BX-41 microscope and Olympus Camedia 3030 digital camera with resolution of 3.3 mega pixel, using Sterlitech Corporation (USA) Polycarbonate membrane filters with pore size of 0.4 micron. Specifically, *E-Coli* DH5Alpha bacteria were imaged with optical microscope with ×40 magnification using green color filter. It is shown that there are darker spots at the edges of the bacteria which are not visualized by most colors. In addition, the dark spots at the edges present special phenomena visualized in some of the *E-coli* bacteria.

FIG. 1B is an image of *E-Coli* DH5Alpha bacteria taken with Olympus BX-41 microscope and Olympus Camedia 3030 digital camera (with ×40 magnification using green color filter). The green color filter induced visualization of darker spots at the edges of the imaged bacteria which are not visualized by other colors. In addition, the dark spots at the farthest edges (or ends) present special visual phenomena (aberration) which appears in some of the *E-coli* DH5Alpha bacteria which are induced by green illumination.

Figure 1C:
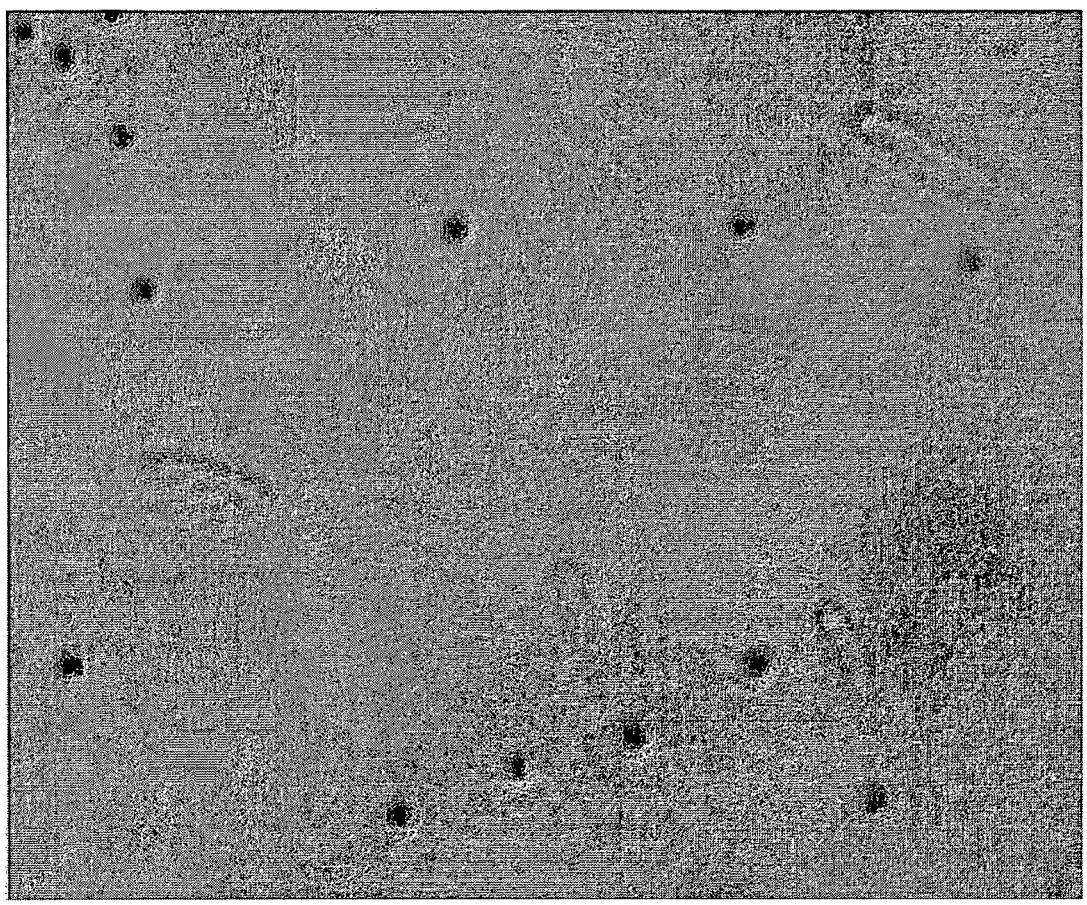
FIG. 1C is an image of the same sample of FIG. 1B, imaged by the same conditions but with white illumination (i.e. without green color filter). It is shown that the dark spots at the edges of the bacteria are not visualized.

FIG. 1C is an image of the same sample of FIG. 1B, imaged by the same conditions but for white illumination (i.e. without green color filter). It is shown that the dark spots at the edges of the bacteria are not visualized.

Figure 2A:
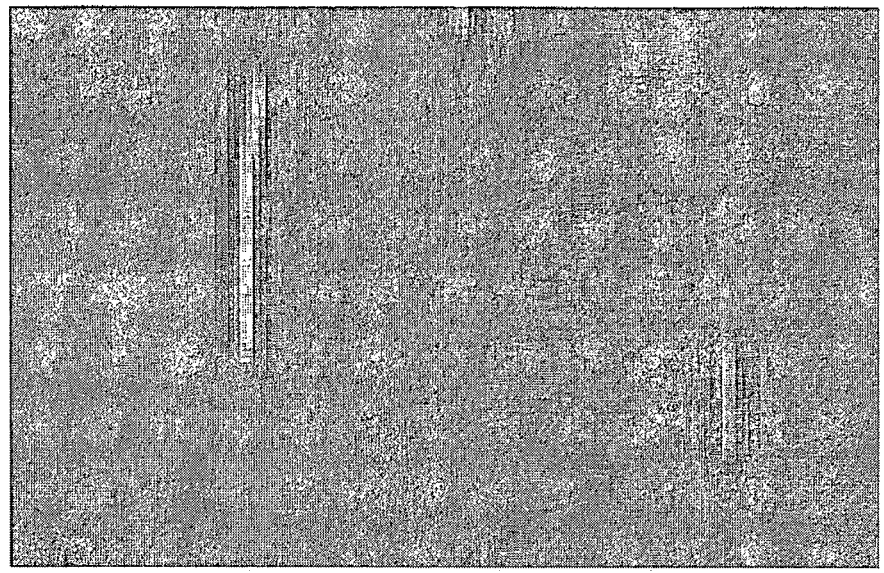
FIGS. 2A-2B are images of *E-Coli* using optical microscope with ×40 magnification using green color filter (FIG. 2A) or red color filter (FIG. 2B), which show a difference in the borders of the bacteria image. The phenomena presented in both images are related to the changes of color of the bacteria and its borders in comparison to the background color which provide the capability to detect the bacteria of interest.
Figure 2B:
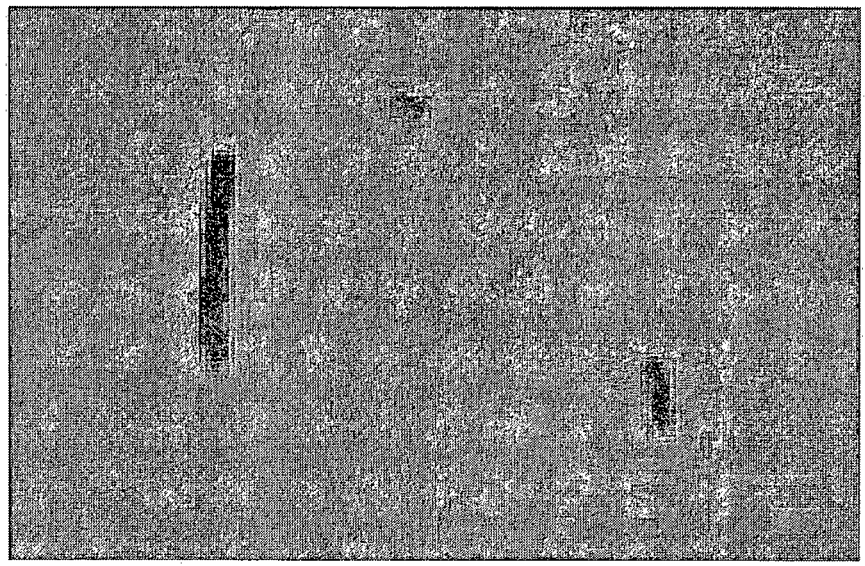

FIG. 2A shows an image of *E-Coli* using optical microscope with ×40 magnification using green color filter. FIG. 2B shows the image of *E-Coli* using optical microscope with ×40 magnification using red color filter. Difference in the borders of the bacteria image is exhibited. The phenomenon presented in the images relates to the changes of color of the particular bacteria which varies depending on the illumination conditions used. Furthermore, the border image of the bacteria if compared to the background color in proximity to the bacteria provides the capability to detect or identify the bacteria of interest.

Figure 3A:
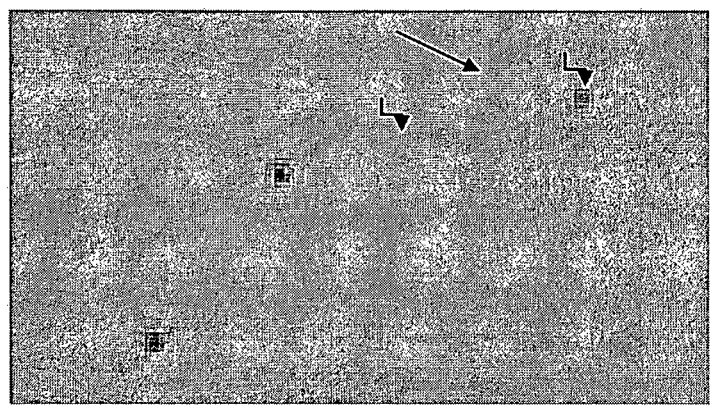
FIGS. 3A-3C are images of mixed populations of bacteria.
Figure 3B:
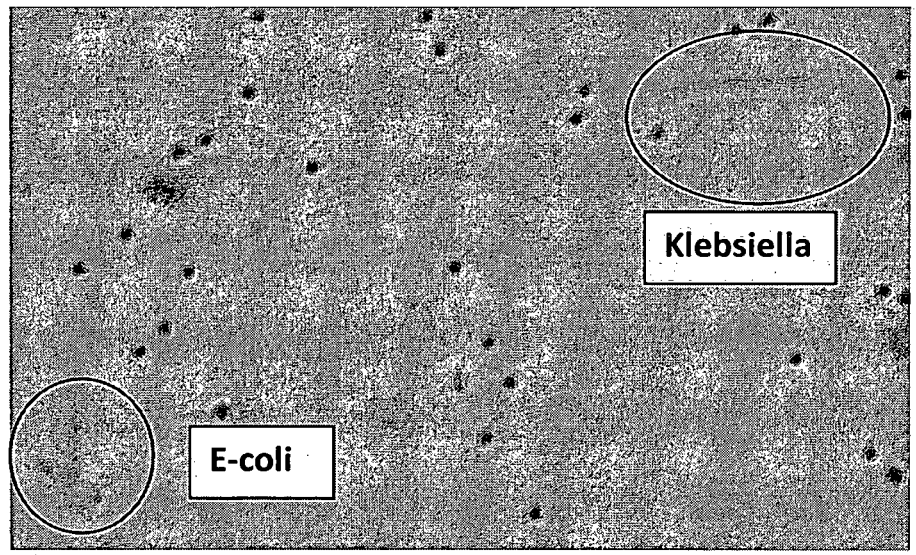
Figure 3C:
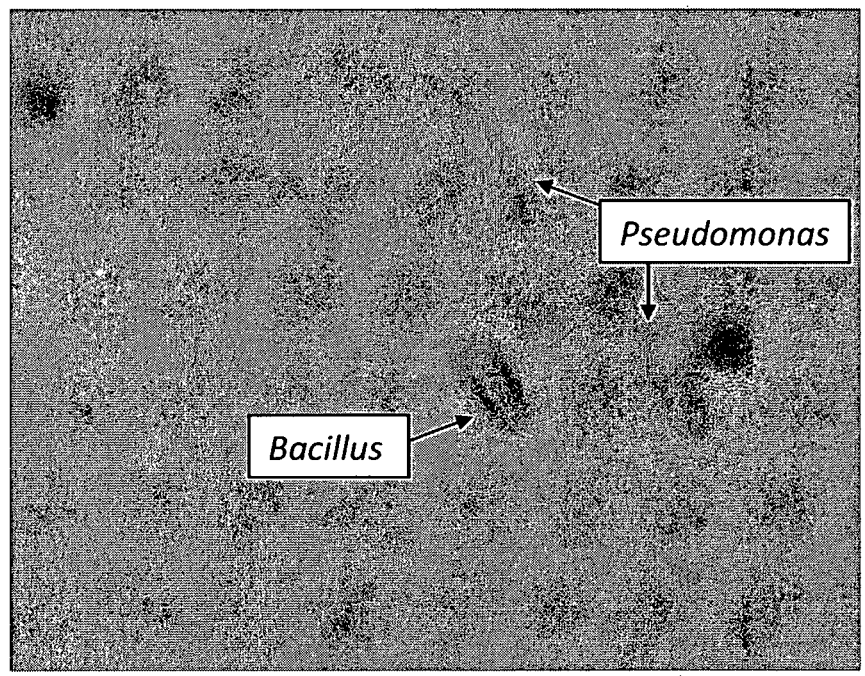

FIGS. 3A-3C are images of mixed populations of bacteria. FIG. 3A is an image of *E-coli* DH5Alpha (see straight arrow) and *Pseudomonas Aeruginosa* (broken arrow) FIG. 3B is an image of *E-coli* DH5Alpha (in bottom left circle) and *Klebsiella Oxytoca* (in upper right circle).

Figure 4:
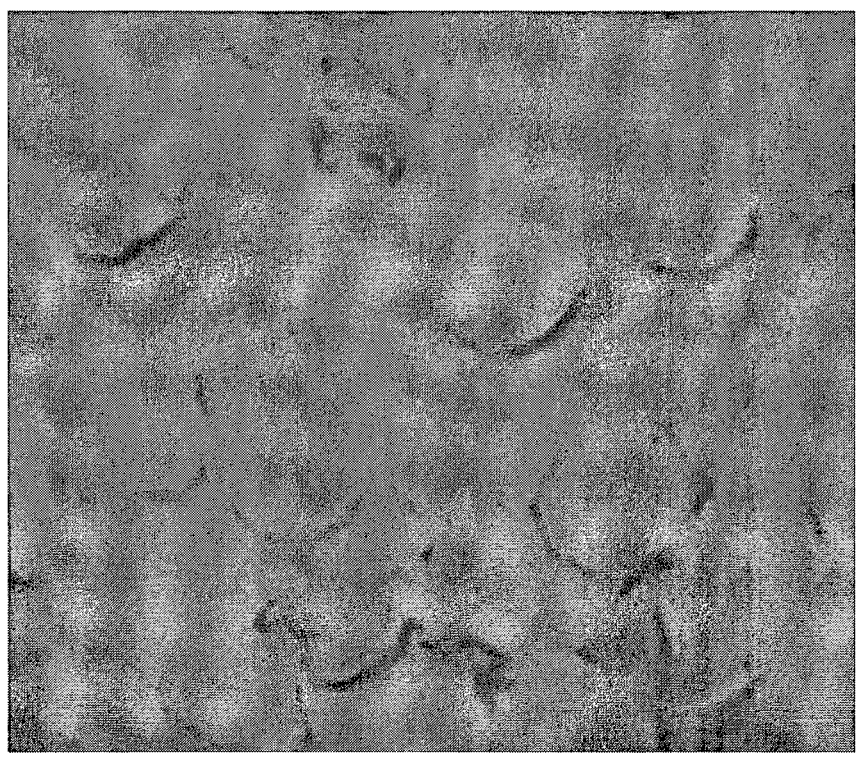
FIG. 4 is an image of a blood sample taken from human subject and placed on a glass slide covered by a 0.17 mm thin glass slip and using Optika 353 Microscope with Sony Cybershot DSC-P92 digital camera. The slide was imaged with a UV filter. It is shown that the white blood cells, located at center to left upper section of the image have different morphology, colors and contrast levels than the red blood cells located at the center to bottom of the image. It is shown that the white blood cells have darker contour, higher contrast to the background and special topology.

FIG. 3C is an image of *Bacillus subtilis* (bottom left) and *Pseudomonas aeruginosa* (upper and right bacteria). These images show that the differences between the bacteria can be viewed by several parameters such as, bacteria dimensions, contour and contrast level surrounding the bacteria and contrast levels within the bacteria body. These parameters allow distinction between the different bacteria types and further enable detection and identification of the bacteria;

FIG. 4 is an image of a blood sample taken from human subject and placed on a glass slide covered by a 0.17 mm thin glass slip and using Optika 353 Microscope with Sony Cybershot DSC-P92 digital camera. The slide was imaged with a UV (390) filter. It is shown that a white blood cell, located at upper center section of the image have different morphology, colors and contrast levels than the red blood cells located at the rest of the image. It is shown that the white blood cell have darker contour, higher contrast to the background and special topology.

Figure 5A:
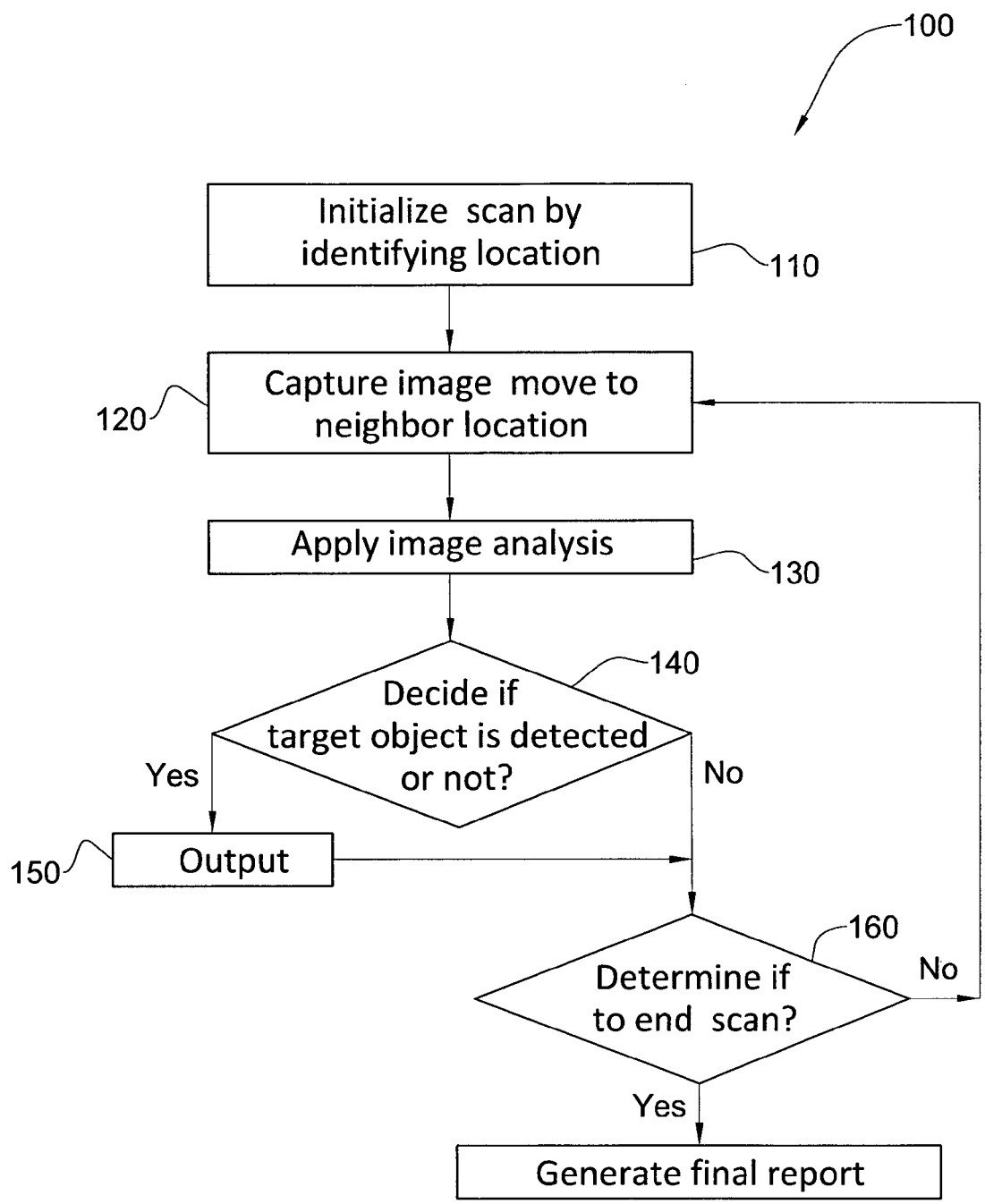
FIGS. 5A-5B are flowcharts exemplifying a method of the present invention for detection and/or identification of target biological object in a sample.

FIG. 5A is a flowchart illustrating a non-limiting embodiment of a method 100 for identifying biological objects. The method 100 comprises an initialization step 110. The initialization step 110 can be used to select or identify the imaging initial location on the substrate i.e. the location on the substrate in which scanning will be initiated. One the location of the substrate is identified, the substrate is illuminated and an optical image of the illuminated substrate is obtained 120. Acquiring the optical image of the illuminated substrate can comprise the step of scanning the sample area or substrate. The scanned area can be the whole sample area or an area of interest.

Illumination comprises illuminating the substrate or a slide carrying the biological objects with a light beam at a wavelength band (not shown). The wavelength band is selected to induce an optical aberration in the acquired image. The optical aberration induced is thus captured in the obtained image. The captured image of step 120 is then subjected to image analysis step 130. Image analysis typically comprises analyses of the captured image to produce an output signal or value (or combination of values) indicative of the presence or absence of an optical aberration in the acquired image. The value or signal produced can be used to decide in a following step 150 whether a suspicious biological object is identified. By way of non-limiting example, the decision making step 140 can be achieved by querying a database comprising an associative data structure which associates optical aberrations with biological objects which are characterized by distinctive or differentiating optical aberrations.

The optical aberrations can also be produced by applying different illumination conditions on the sample area or the substrate. If the decision provides a YES result, namely that a suspicious biological object is detected or identified, output signal is produced in following step 150 which indicates that a biological object was detected on the substrate. If the decision provides a NO result, namely, that a suspicious biological was not identified, an additional image of the sample area can be produced by returning to image capturing step 120, with different illumination conditions in order to induce either the same or different optical aberration. Optionally, if a suspicious biological was not identified (NO result), a determination can be made 160 according to which scan is to be terminated or continued at a neighboring location on the sample area. Prior to termination of the scanning method 100 a final report can be issued 170. Typically, a final report is generated 170 will include indications or otherwise information indicative of the biological objects which were detected on the substrate.

Figure 5B:
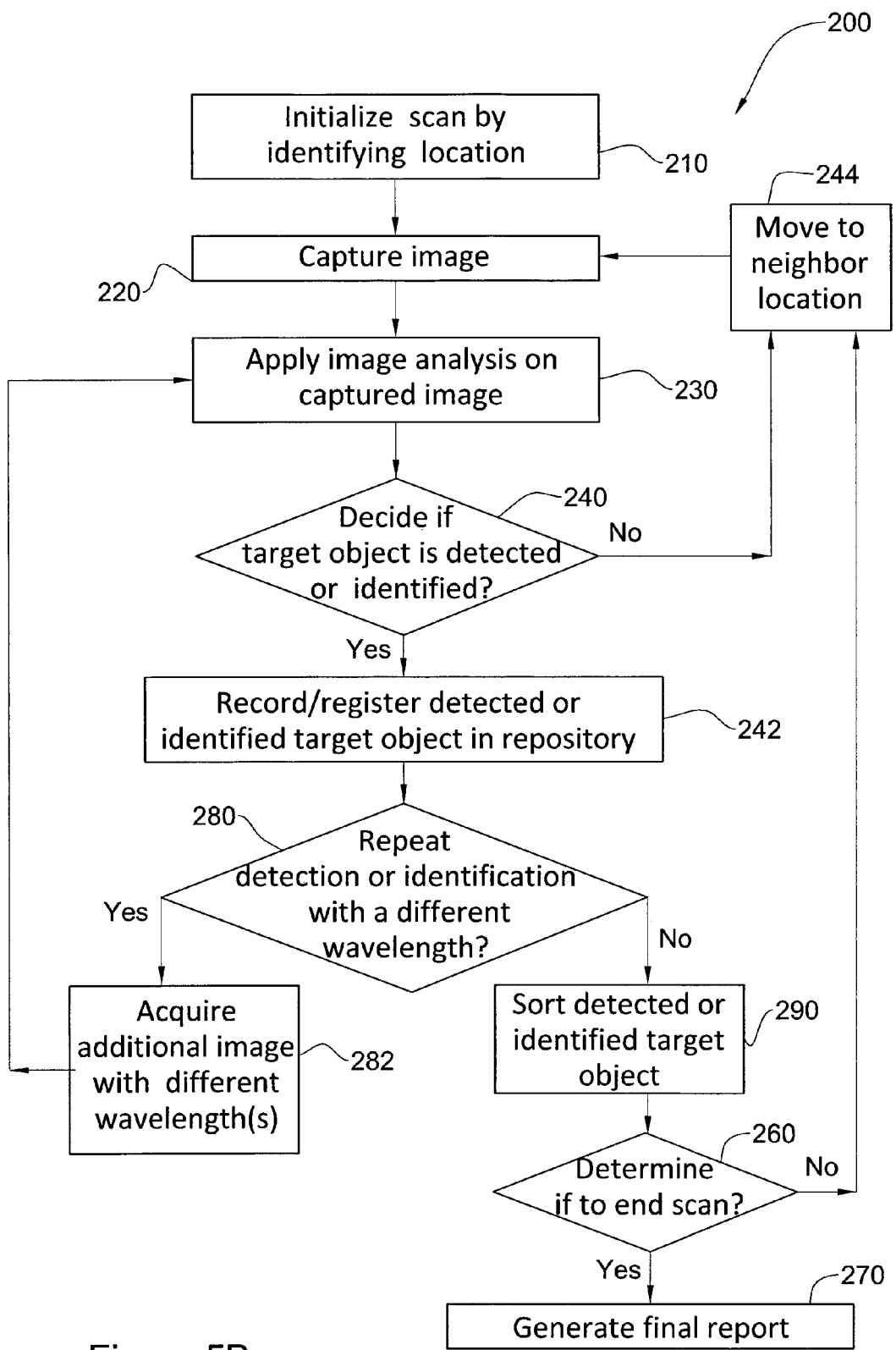

Reference is now made to FIG. 5B which illustrates an additional non-limiting embodiment of the method for identifying biological objects. For simplicity, like reference numerals to those used in FIG. 5A, shifted by 100 are used to identify components having a similar function. For example, component 110 in FIG. 5B is an initialization step 210 having the same function as initialization step 110 in FIG. 5A.

Following a YES result in the decision step 240, the detected biological object can be stored in a repository 242. By way of non-limiting example, the repository can be a database which is operable to provide storage and retrieval of information such as the identity of the biological object, optical aberration and/or illumination conditions associated therewith. If a biological object was not detected (NO result in decision step 240), the area of interest can be shifted in step 244, to a neighboring location on the sample area, where a further capturing step 220 takes place.

The method 200 can further include a step of determining whether additional images are required (not shown). For example, additional images of the sample area may be required if the optical aberration being identified is insufficient to determine identity of the biological object with sufficient amount of confidence. The confidence level can be represented, for example, by a probability threshold for the presence of the biological object. The method 200 can further comprise determining whether additional images are required at a different wavelength 280 (or other illumination conditions). If YES, additional images are acquired at step 282, at e.g. different wavelengths.

The results, including the detected or identified target objects can be sorted 290. Optionally, a determination step 265 can be made according to which scan is to be terminated (YES) or continued (NO) at a neighboring location on the sample area 244. At termination, a final report can be issued 270.

It is within the scope of the present invention that different applications may require different sorting of the detected or reported biological objects. For example, in some applications the presence of *E. coli* in the sample area is more important than the presence of another biological object. Therefore, the order of the detected biological objects can be performed in accordance of the respective importance of the biological object.

Figure 6:
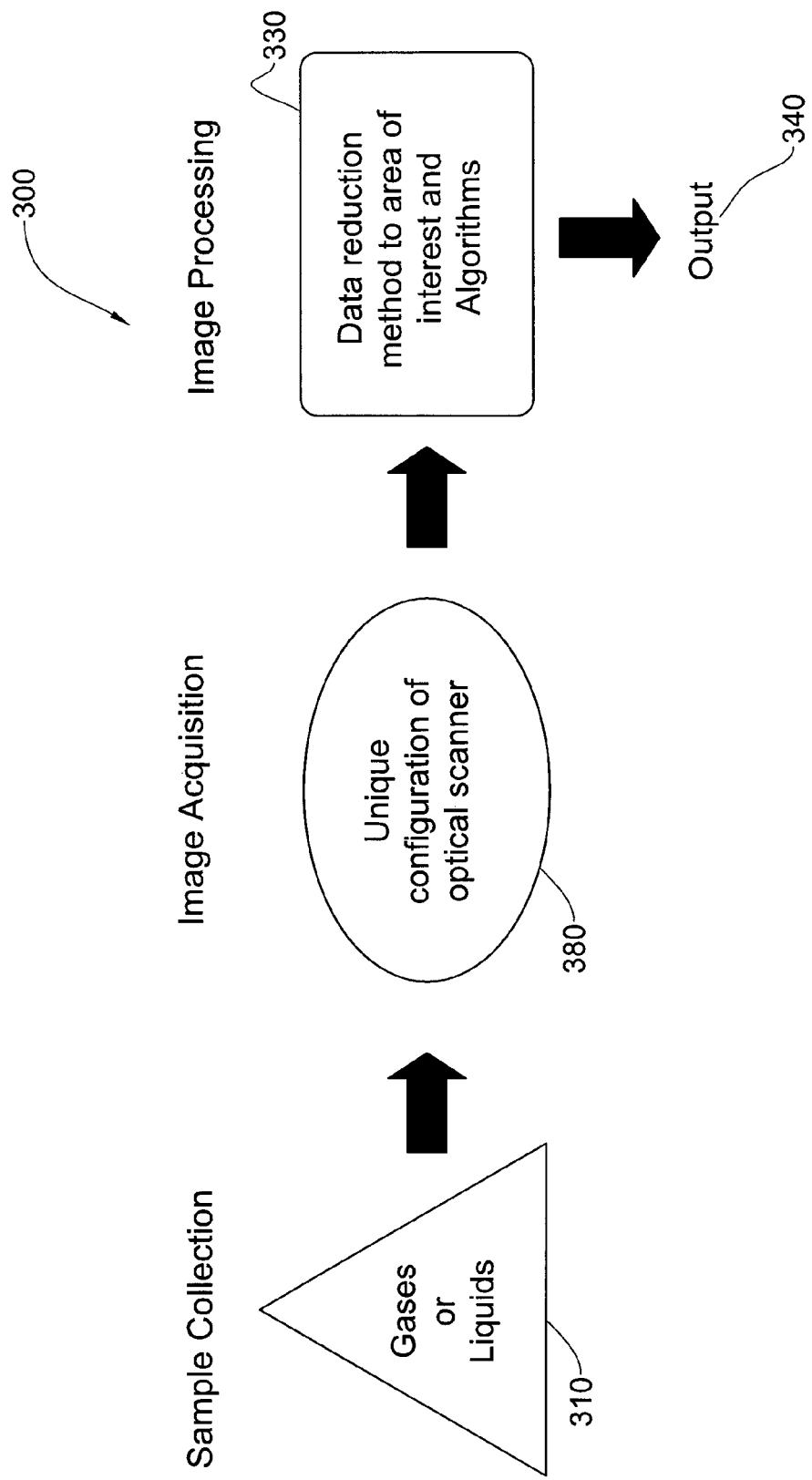
FIG. 6 is a block diagram of a system of the invention detection and/or identification of target biological object in a sample.

FIG. 6 provides a schematic illustration of a system 300 in accordance with one embodiment of the present invention. The system 300 includes a sample collection apparatus or other collection means 310 for collecting samples that may be in a gas or liquid state. The system 300 further comprises image acquisition apparatus 320. The image acquisition apparatus 320 typically includes an optical scanner. The system 300 also comprises image processing module or apparatus 330, used to analyze the captured images of the sample area or substrate which carry the biological objects. The system 300 may comprise an output module 340 which is operable to provide detection, identification and/or quantification of the biological object detected.

Figure 7:
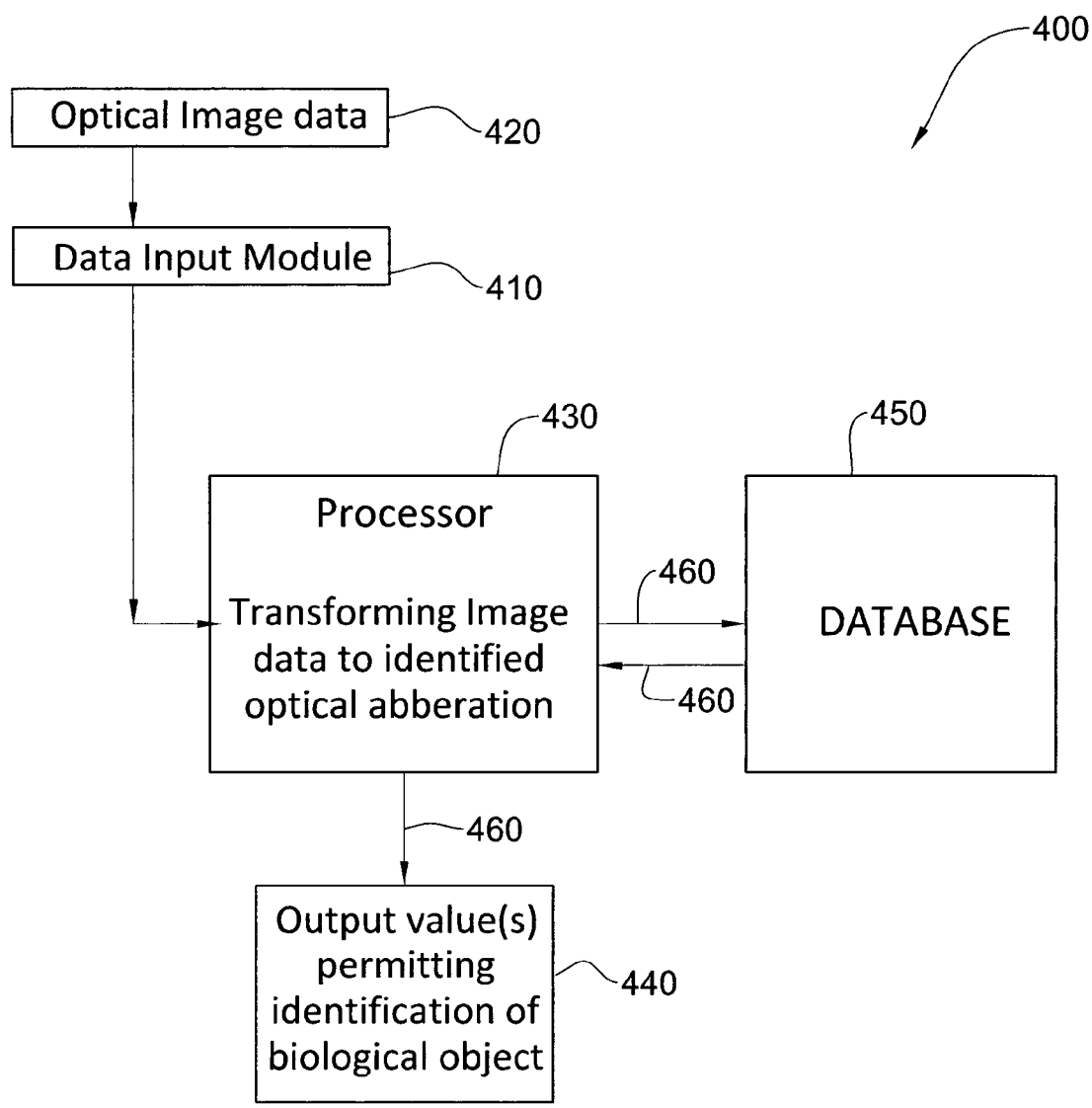
FIG. 7 is a block diagram of a processing unit for identifying biological objects in a sample.

Reference is now made to FIG. 7 which provides a schematic block diagram of a processing unit (sub-system) according to one embodiment of the invention. The processing unit 400 is used for identifying biological objects in a collected gas or liquid sample. The processing unit 800 comprises input module 410 configured and operable to receive data corresponding to an optical image 420 of a substrate supporting the sample. The processing unit 400 can also comprise a processor 430 configured and operable to process the optical image and in turn output a single, or a value or a combination of signals/values 440 indicative of presence or absence of at least one optical aberration in the acquired optical image.

In some embodiments, the processor 430 communicates with a database 450 comprising inter alia, data regarding optical aberrations associated with biological objects.

The various components of system 400 may be communicated via communication channels 495. In this respect, any communication protocol can be used e.g. wireless, RF, IR and the like. By way on non-limiting example, database 450 can be fed or provided with the optical aberration being identified by processor 430 and retrieve the biological objects which are associated with the detected optical aberrations.

Figure 8:
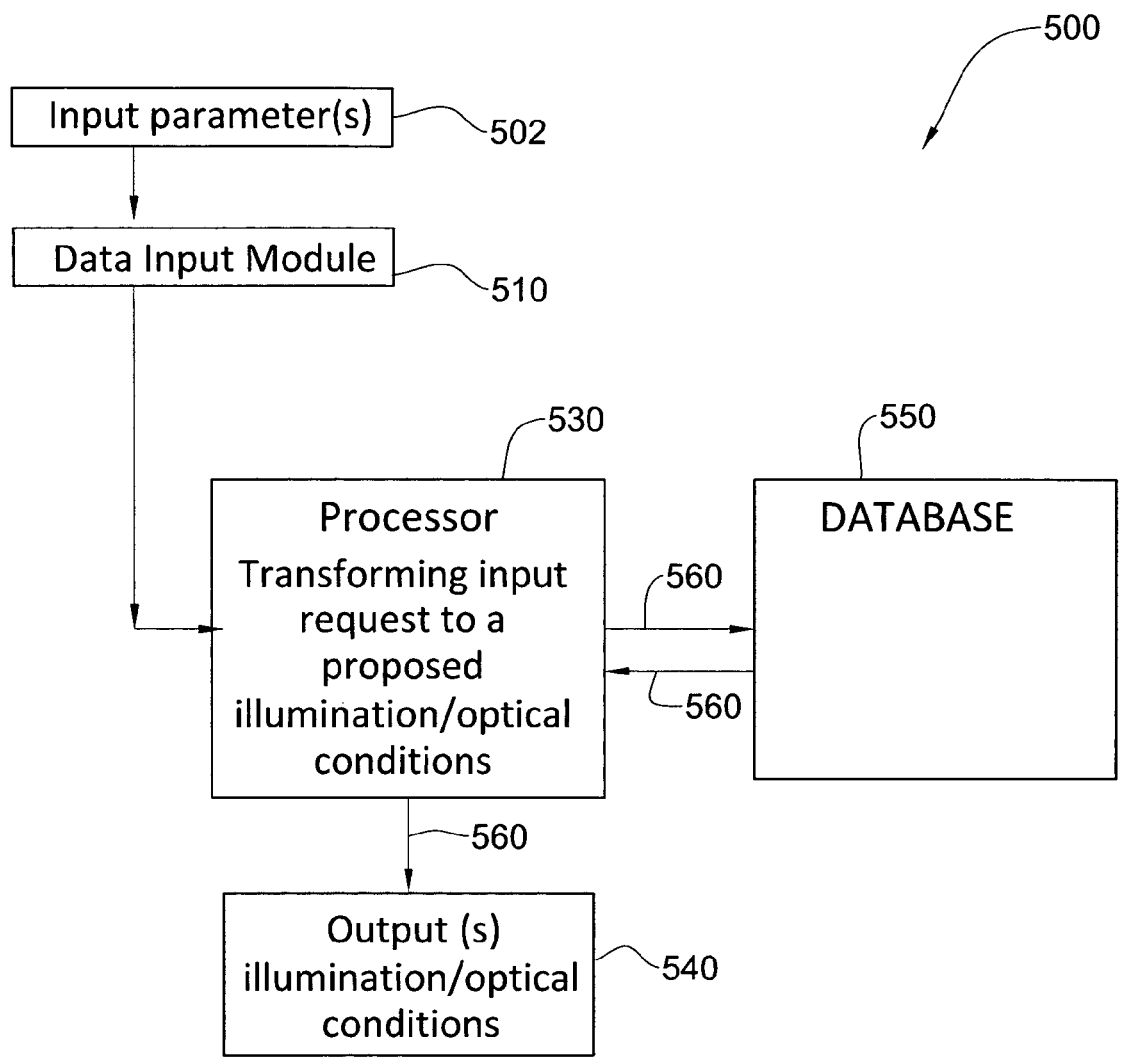
FIG. 8 is a block diagram illustrating a processing unit for determining an illumination condition which matches or is associated with a desired optical aberration and/or a biological object.

Reference is now made to FIG. 8 which provides a schematic block diagram of a processing unit (sub-system) 500, in accordance with another embodiment of the invention. For simplicity, like reference numerals to those used in FIG. 7, shifted by 100 are used to identify components having a similar function. For example, data input module 410 in FIG. 7 has the same function as data input module 510 in FIG. 8.

Processing unit 500 can be used to determine an illumination condition which matches or is associated with a desired optical aberration and/or a biological object of interest. The illumination condition thus determined can be used to induce the desired optical aberration in an imaged biological object.

The processing unit 500 comprises a data input module 510 configured and operable to receive a parameter of a biological object (as described hereinbefore) or a desired optical aberration being associated with said parameter. The processing unit 500 can also comprise a processor 530 which can be configured and operable to process the input parameter of a biological object or the desired optical aberration 502 and provide an illumination condition which can be affected to induce the desired optical aberration in the imaged biological object. A system such as that illustrated in FIG. 6 typically requires an initialization hardware or process. Initialization can take the form of providing the processing unit 500 with pre-determined settings adjusted for the specific application or the specific biological objected to be detected. Optionally, the pre-determined settings are determined by the operator/user (not shown).

In some embodiments, the processor 530 communicates with a database 550. The processing unit is equipped with communication links 595. In this respect, any communication protocol can be used to link between the various components of this sub-system, e.g. wireless, RF, IR and the like. By way on non-limiting example, database 550 can be queried with desired optical aberration and/or a parameter or a biological object. The processor 530 thus receives from the database the optional illumination conditions which are associated with the desired optical aberrations.

Figure 9:
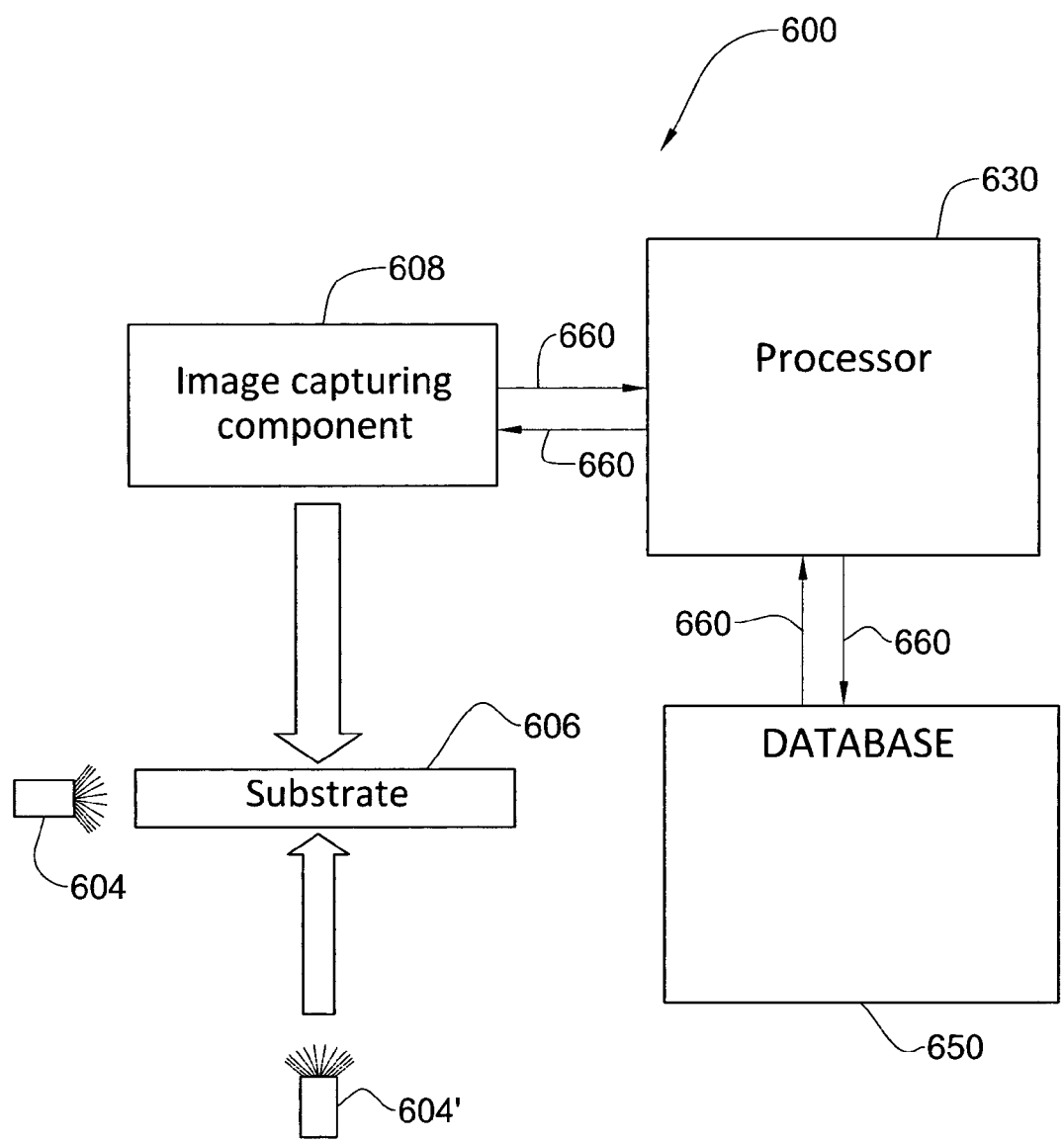
FIG. 9 is a schematic block diagram of a system for identifying biological object in an obtained sample.

Reference is now made to FIG. 9 provides a block diagram of a further system 600 for identifying biological object in an obtained sample, in accordance with another embodiment of the invention. For simplicity, like reference numerals to those used in FIG. 7, shifted by 200 are used to identify components having a similar function. For example, data input module 410 in FIG. 7 has the same function as data input module 610 in FIG. 8.

The system 600 comprises a light source (604 and/or 604'), configured and operable to illuminate the sample placed on substrate 606. The light source (604 and/or 604') may be provided with selective wavelengths illumination. The light source can be responsive to a signal indicating an illumination condition required (not shown). In response to receiving the signal indicating the illumination condition, the light source (604 and/or 604') is operable to illuminate the obtained sample under selected illumination condition. As schematically illustrated, system 600 may comprise two illumination sources, namely, side light illumination source 604 and backlight illumination source 604'. The system 600 also comprises an image capturing component 608. The image acquiring component 608 is configured and operable to acquire an optical image of the objects in the sample which is maintained or carried on the substrate 606.

The system 600 further comprises a processor 630 configured and operable to process the acquired optical image. The system 600 further comprises communication links 660 that can be any one known communication means including wireless communication, RF and the like. In response to the received captured image, the processor 630 outputs a value or a combination of values indicative of presence or absence of an optical aberration in the acquired image. In some embodiments, the processor 630 communicates with a database 650 through a communication link 660. By way on non-limiting example, database 650 can be fed or provided with the optical aberration being identified by processor 630 and retrieve the biological objects which are associated with the detected optical aberrations.

The invention claimed is:

1. A method for identifying biological objects on a substrate, comprising:
    illuminating the substrate carrying the biological objects under illumination conditions that induce at least one optical aberration in an optical image of the biological object, which optical aberration is not seen using only white illumination, wherein said illumination conditions comprise illumination with a light beam having a wavelength band with a width of about 100 nm or narrower;
    acquiring at least one optical image of the illuminated substrate including said at least one optical aberration; and
    processing said at least one optical image to provide a value or a combination of values indicative of presence or absence of said at least one optical aberration, said value or combination of values permitting detection or identification of the biological objects on said substrate.

2. The method of claim 1, wherein said wavelength band is within the infra-red (IR) spectrum, the ultra-violet (UV) spectrum or the visible (VIS) spectrum.

3. The method of claim 1, wherein said wavelength band is a narrow band having a width in the range of between about 10 nm to about 100 nm.

4. The method of claim 1, wherein said light beam is a single light beam.

5. The method of claim 1, wherein said biological object is carried on a substrate and said illumination conditions further comprise a backlight or a sidelight illumination with respect to said substrate or a combination of backlight and sidelight illuminations with respect to said substrate.

6. The method of claim 1, wherein said optical aberration comprises one or more of blurring of at least a portion of an imaged biological object, hue or color change of at least a portion of an imaged biological object, structure enhancement of structural features, structure changes or distortions, or change of gray levels of at least a portion of an imaged biological object.

7. The method of claim 1, wherein the biological objects have an average size of between 0.4 to 200 µm.

8. The method of claim 1, wherein the biological object is a eukaryotic or a prokaryotic cell.

9. The method of claim 8, wherein said biological object is a prokaryotic cell selected from the group consisting of *Escherichia coli, Salmonella, Pseudomonas, Klebsiella, Chlamydia, Staphylococcus*, or *Streptococcus*.

10. The method of claim 8, wherein said biological object is a eukaryotic cell selected from the group consisting of mammalian, fungal and plant cells.

11. The method of claim 1, wherein said processing comprises any one of image analysis of one or more images acquired from said illuminated substrate, image analysis of two or more images acquired from a sample illuminated with the same light beam or two or more light beams characterized by a different wavelength or different wavelength bands.

12. The method of claim 1, further including the steps of illuminating the substrate carrying the biological objects under second illumination conditions, which second illumination conditions induce at least one optical aberration in an optical image of the biological object, which optical aberration is not seen using only white illumination, wherein said second illumination conditions comprise illumination with a light beam having a wavelength band of about 100 nm or narrower, wherein the two illumination conditions are selected so as to induce different optical aberrations, and acquiring at least one optical image of the illuminated substrate at the second illumination conditions, wherein said processing step comprises processing the optical images obtained at each of the illumination conditions to provide a value or a combination of values indicative of presence or absence of said two optical aberrations, and analyzing the images acquired using different illumination conditions to permit detection or identification of the biological objects on said substrate.

13. The method of claim 1, wherein said processing comprises comparing said value or combination of values indicative of said aberration with a database comprising optical aberrations characterizing a biological object.

14. The method of claim 13, wherein said comparing provides identification of at least one member of the group of biological objects consisting of a biological species or a biological family of organisms.

15. The method of claim 1, further including the steps of illuminating the substrate carrying the biological objects under said illumination conditions at a different time point within a predefined time window, and acquiring at least one optical image of the illuminated substrate at the second time point, wherein said processing step comprises processing said optical images obtained at each time point to provide a value or a combination of values indicative of presence or absence of said at least one optical aberration, and analyzing the images acquired at different time points to permit detection or identification of the biological objects on said substrate and to obtain therefrom a time dependent value or combination of values indicative of a state of said biological object.

16. The method of claim 15, wherein said state of said biological object comprises a parameter selected from the group consisting of viability; location; arrangement of said biological object structure or organelles; reproducibility; motility; shape; motility speed and shape; transparency; thickness; and mutual behavior of biological objects.

17. The method of claim 1, wherein said illumination conditions further comprise a variation of illumination intensity as compared to the illumination intensity using only white illumination at which no optical aberration is seen.

18. The method of claim 1, wherein said illumination conditions comprise a variation of the light source from the source of white illumination at which no optical aberration is seen when using only that source of white illumination.

19. The method of claim 1, wherein said illumination conditions comprise the use of a filter.

20. The method of claim 1, wherein said illumination conditions comprise the use of LED with selected color.

21. The method of claim 1, wherein said illumination conditions comprise the use of micro-optics with prisms.

22. The method of claim 1, wherein the method is for detecting and identifying biological contamination in gases or liquids, wherein said biological object is obtained from a sample of the gas or liquid being tested.

23. The method of claim 1, wherein the method is for detection of undesired biological objects in a bodily fluid or in a bodily tissue, wherein said biological object is obtained from the bodily fluid or a bodily tissue being tested.

24. The method of claim 1, wherein said biological object is a microbial cell.

25. The method of claim 1, wherein a plurality of illumination conditions are used, wherein each of said illumination conditions comprises illumination with a light beam having a wavelength band with a width of about 100 nm or narrower, to determine which best produces said optical aberration, and wherein said acquiring and processing steps are conducted with the illumination condition that best produces said optical aberration.

* * * * *